(12) United States Patent
Liu et al.

(10) Patent No.: US 8,478,385 B2
(45) Date of Patent: Jul. 2, 2013

(54) ROTARY MEDICAL MANIFOLD

(75) Inventors: Yunxing Liu, Maplewood, MN (US); Chun Li, BeiJing (CN)

(73) Assignee: United Medical Innovations, Inc., Maplewood, MN (US)

( * ) Notice: Subject to any disclaimer, the term of this patent is extended or adjusted under 35 U.S.C. 154(b) by 924 days.

(21) Appl. No.: 12/562,996

(22) Filed: Sep. 18, 2009

(65) Prior Publication Data
US 2011/0071390 A1   Mar. 24, 2011

(51) Int. Cl.
*A61B 5/00* (2006.01)
*A61M 5/00* (2006.01)

(52) U.S. Cl.
USPC .............. 600/432; 604/30; 604/32; 604/80; 604/247

(58) Field of Classification Search
USPC .............. 600/432; 604/30, 32, 80; 137/255, 137/263, 266; D24/129
See application file for complete search history.

(56) References Cited

U.S. PATENT DOCUMENTS

| | | |
|---|---|---|
| 3,157,201 A | 11/1964 | Littmann |
| 3,774,604 A | 11/1973 | Danielsson |
| 3,834,372 A | 9/1974 | Turney |
| 4,769,017 A | 9/1988 | Fath et al. |
| 4,915,688 A | 4/1990 | Bischof et al. |
| 5,019,054 A | 5/1991 | Clement et al. |
| 5,074,334 A | 12/1991 | Onodera |
| 5,084,031 A | 1/1992 | Todd et al. |
| 5,097,840 A | 3/1992 | Wallace |
| 5,104,387 A | 4/1992 | Pokorney et al. |
| 5,168,901 A | 12/1992 | Marks |
| 5,232,024 A | 8/1993 | Williams |
| 5,288,290 A | 2/1994 | Brody |
| 5,328,463 A | 7/1994 | Barton et al. |
| 5,423,751 A | 6/1995 | Harrison et al. |
| 6,135,153 A | 10/2000 | Cleland, Sr. |
| 6,158,467 A | 12/2000 | Loo |
| 6,457,488 B2 | 10/2002 | Loo |
| 6,976,974 B2 | 12/2005 | Houde et al. |
| 7,153,288 B2 * | 12/2006 | Duchon et al. ................. 604/110 |
| 7,172,572 B2 | 2/2007 | Diamond et al. |
| 2004/0221904 A1 | 11/2004 | Usher et al. |
| 2008/0167621 A1 | 7/2008 | Wagner et al. |
| 2009/0171279 A1 * | 7/2009 | Brumleve et al. .......... 604/99.04 |

* cited by examiner

*Primary Examiner* — Unsu Jung
*Assistant Examiner* — Phong K Huynh
(74) *Attorney, Agent, or Firm* — Schwegman Lundberg Woessner P.A.

(57) ABSTRACT

A rotary medical manifold, for delivering various fluids through a patient delivery mechanism is described. The rotary manifold can include a manifold body and a valve stem. The manifold body can include a central cavity, an output port, a first fluid port, and a second fluid port. The valve stem can include an injector port, and a single central fluid passage. The valve stem can be adapted to slidably engage the central cavity of the manifold body and provide selective fluidic connectivity between the injector port and the output port, the first fluid port and the second fluid port.

21 Claims, 11 Drawing Sheets

ROTARY MEDICAL MANIFOLD

BACKGROUND

Medical procedures often involve injecting a patient with multiple different fluids through a needle, catheter, or some similar patient delivery mechanism. Some medical procedures benefit from the ability to inject multiple fluids without disconnecting the patient delivery mechanism. One such medical procedure is angiography. Angiography is a medical imaging procedure used to visualize the inside of blood vessels and organs of the body. Often, angiography is used to detect blocked or narrowed blood vessels, typically in and around a patient's heart. Angiographic procedures require the injection of r radiographically opaque contrast medium (also commonly referred to as contrast agents) into a patient's vascular system. In angiography, the contrast agent is injected into the vascular system through a catheter positioned near the area of interest within the patient's body. The contrast agent is added to the blood to make the vessels visible on the x-ray images taken once the contrast agent is administered.

The contrast agent is normally injected from a manually-operated syringe into an attached medical manifold, which provides fluidic connections to a catheter, contrast agent supply, and often a saline solution supply. Connections between the manifold, syringe and catheter are typically made with a threaded connector, typically a Luer Taper connector.

Commonly used medical manifold include multiple individual valves for each fluid source connected to the manifold. For example, in a typical angiographic procedure the contrast fluid, saline, and patient delivery mechanism will each have at least one valve associated with each respective connection to the manifold. The procedure requires the physician to properly open and close each individual valve in the proper sequence.

OVERVIEW

The present inventor has recognized, among other things, that the current medical manifold in common use require a complicated series of valve manipulations to complete a routine medical procedure such as angiography. The present inventor has also recognized, among other things, that the medical manifold current on the market can be expensive to manufacture and uses more material than is necessary, increasing the amount of medical waste generated by routine medical procedures.

Example 1 includes a manifold body, a valve stem, and An optional dial. The manifold body can include a central cavity, an output port, a first fluid port, and a second fluid port. The valve stem can be adapted to slidably engage the central cavity and include a single central longitudinal fluid passage, a first perpendicular fluid passage and a second perpendicular fluid passage. The single central longitudinal fluid passage can be coupled to an injector port. The first perpendicular fluid passage can intersect the central longitudinal fluid passage to selectively provide fluidic transport between the central longitudinal fluid passage and the output port when the valve stem is in a first rotational position. The second perpendicular fluid passage can intersect the central longitudinal fluid passage to selectively provide fluidic transport between the central longitudinal fluid passage and a selected one of the first and second fluid ports, fluidic transport to the first fluid port is provided when the valve stem is in a second rotational position and fluidic transport to the second fluid port is provided when the valve stem is in a third rotational position. The dial can be coupled to the valve stem and can be adapted to enable selective rotation of the valve stem within the central cavity to rotatably selectively provide fluidic transport between the central longitudinal fluid passage and one of the first fluid port, the second fluid port, and the output port.

In Example 2, the apparatus of Example 1 optionally includes the manifold body including a self-biasing mechanism to positively position the valve stem in the first, the second, or the third rotational position. The self-biasing mechanism can include a plurality of detent cavities, a detent ball, and a detent bias member. The plurality of detent cavities positioned in each of the first, second, and third rotational positions. The detent ball configured to inhibit rotational movement of the valve stem when positioned within one of the detent cavities. The detent bias member configured to press the detent ball into one of the detent cavities.

In Example 3, the apparatus of one or any combination of Examples 1-2 optionally include a valve stem comprising a stepped cylinder with a first cylinder diameter at the output port position, and a second cylinder diameter at the first and second fluid port position.

In Example 4, the apparatus of one or any combination of Examples 1-3 optionally include a manifold body including the pressure transducer port selectively coupled in fluid communication with the output port and configured to be coupled to a pressure transducer to permit monitoring of fluid pressure at the output port. The valve stem also includes a transducer fluid passage.

In Example 5, the apparatus of one or any combination of Examples 1-4 optionally includes a transducer fluid passage having a semi-circular groove in a perimeter of the valve stem.

In Example 6, the apparatus of one or any combination of Examples 1-5 optionally includes a transducer fluid passage configured to inhibit or prevent exposing the pressure transducer to fluid pressure from the injector port.

In Example 7, the apparatus of one or any combination of Examples 1-6 optionally includes a valve stem that is adapted to snap-fit into the central cavity of the manifold body.

In Example 8, the apparatus of one or any combination of Examples 1-7 optionally includes a gas bubble detector coupled to the output port and configured to detect a gas bubble in a fluid exiting the output port.

In Example 9, the apparatus of one or any combination of Examples 1-8 optionally includes a gas bubble detector configured to detect a gas bubble by detecting a change in a light wave passing through the fluid exiting the output port.

Example 10 includes a fluid delivery system, the system comprising a manifold configured to selectively interconnect, using a central rotary valve, an injector port with a first fluid port, a second fluid port, and a patient delivery port, the central rotary valve having a single central longitudinal fluid passage. The first fluid port can be configured to be coupled to a contrast fluid source. The second fluid port can be configured to be coupled to a saline fluid source. The injector port can be configured to be coupled to an injection device. The injection device is configured to draw in fluid and output fluid. The injection device can draw fluid from the contrast source when the central rotary valve is in a first rotational position. The injection device can draw fluid from the saline source when the central rotary valve is in a second rotational position. The injection device can output fluid through the patient delivery port when the central rotary valve is in a third rotational position.

In Example 11, the system of Example 10 optionally includes a pressure transducer connected to a pressure transducer port on the manifold.

In Example 12, the system of one or any combination of Examples 10-11 optionally includes a manifold configured to interconnect the patient delivery port with the pressure transducer port when the central rotary valve is in any one of the first or second rotational position.

In Example 13, the system of one or any combination of Examples 10-12 optionally includes a gas bubble detector coupled to the patient delivery port.

In Example 14, the system of one or any combination of Examples 10-13 optionally includes a gas bubble detector configured to detect gas bubbles in the fluid exiting the patient delivery port by detecting changes in light waves passed through the fluid.

In Example 15, the system of one or any combination of Examples 10-14 optionally includes at least one of the contrast source, the saline source, or the injection device.

Example 16 is a method for using a rotary manifold in a medical imaging procedure and includes the following operations. Providing a rotary manifold with a central rotary valve, an injector port, an output port, a first fluid port, and a second fluid port, the central rotary valve including a single central longitudinal fluid passage connected to the injector port. Connecting a first fluid source to the first fluid port. Connecting a second fluid source to the second fluid port. Connecting a syringe to the injector port of the rotary manifold. Connecting a patient delivery mechanism to the output port. Selecting a first rotational position, of the central rotary valve, the first position interconnecting the first fluid source and the syringe. Drawing fluid from the first fluid source into the syringe. Selecting a second rotational position, of the central rotary valve, the second position interconnecting the syringe and the output port. Ejecting the fluid from the first fluid source from the syringe into the patient delivery mechanism through the output port. Selecting a third rotational position, of the central rotary valve, the third position interconnecting the syringe and the second fluid source. Drawing fluid from the second fluid source into the syringe. Selecting the second rotational position, of the central rotary valve. Ejecting the fluid from the second fluid source from the syringe into the patient delivery mechanism through the output port.

In Example 17, the method of Example 16 optionally includes selecting a fourth rotational position, of the central rotary valve, the fourth position interconnecting the output port with a pressure transducer port. As well as, monitoring pressure from the patient delivery mechanism.

In Example 18, the method of one or any combination of Examples 16-17 optionally includes wherein the second position of the central rotary valve sealing off the pressure transducer port from the output port and the injector port.

In Example 19, the method of one or any combination of Examples 16-18 optionally includes wherein each of the first, second, and third rotational positions are substantially 90 degrees of rotation apart.

In Example 20, the method of one or any combination of Examples 16-19 optionally includes wherein the ejecting the fluid includes monitoring the output port for gas bubbles.

In Example 21, the method of one or any combination of Examples 16-20 optionally includes wherein the monitoring the output port for gas bubbles includes detecting changes in the wavelengths of light passed through the fluid ejected into the patient delivery mechanism.

This overview is intended to provide an overview of subject matter of the present patent application. It is not intended to provide an exclusive or exhaustive explanation of the invention. The detailed description is included to provide further information about the present patent application.

BRIEF DESCRIPTION OF THE DRAWINGS

In the drawings, which are not necessarily drawn to scale, like numerals may describe similar components in different views. Like numerals having different letter suffixes may represent different instances of similar components. The drawings illustrate generally, by way of example, but not by way of limitation, various embodiments discussed in the present document.

DETAILED DESCRIPTION

As described above, some medical procedures, such as angiography, require injecting various fluids into a patient through a catheter or similar device. As described above, an angiographic procedure using a standard medical manifold can require manipulating multiple valves to switch between the various fluids and patient delivery mechanism. The following rotary manifold simplifies the procedure of switching between fluid sources and can provide additional functionality, such as pressure sensing and gas bubble detection.

Rotary Manifold System

Figure 1:
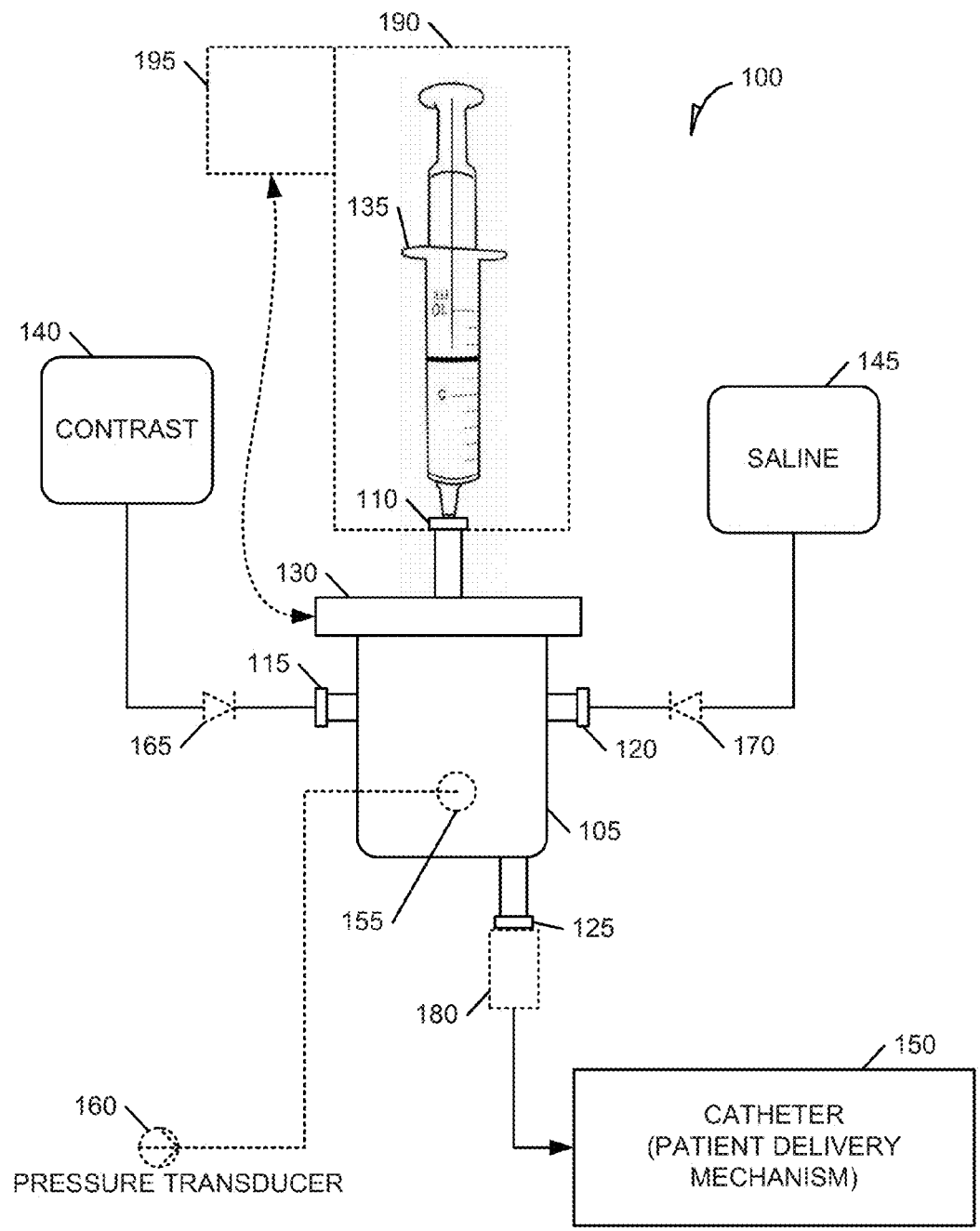
FIG. 1 is block diagram of an example system for injecting multiple fluids using a rotary manifold.

FIG. 1 is block diagram of an example system 100 for injecting multiple fluids using a rotary manifold. The system 100 can include a rotary manifold 105, an injector 135, a contrast agent source 140, a saline source 145, and a patient delivery mechanism 150. In an example, the rotary manifold 105 can include an injector port 110, a first fluid port 115, a second fluid port 120, an output port 125, and a dial 130. In certain examples, the rotary manifold can also include a pressure transducer port 155. In some examples, the system 100 can include a pressure transducer 160 connected to the pressure transducer port 155. In an example, the system 100 can also include a gas bubble detector 180 coupled to or integrated with the output port 125. In certain examples, the contrast source 140 and the saline source 145 are connected to the rotary manifold 105 through one-way check values 165, 170.

In an example, the injector 135 is connected to the rotary manifold 105 through the injector port 110. In some examples, the injector 135 can be a manually operated syringe. As will be discussed in more detail below, the injector 135 can be used to draw fluid from a fluid source (e.g., contrast agent source 140 or saline source 145) and subsequently inject fluid into the patient delivery mechanism 150 through the rotary manifold 105. In other examples, the injector 135 can be a powered injector 190, which may or may not use a manual syringe as part of the mechanism. In certain examples, the powered injection 190 can include a computerized controller 195. The computerized controller 195 can control a motorized version of the rotary manifold 105. In the motorized rotary manifold 105 example, the dial 130 can incorporate an indexing stepper motor (or some similar device) to move the valve stem within the rotary manifold 105 to select different fluidic connectivity options provided by the rotary manifold 105. The computerized controller 195 can work in conjunction with the powered injector 190 to automate the process of injecting fluids using the rotary manifold 105.

In an example, the contrast agent source 140 can be connected to the rotary manifold 105 through the first fluid port 115. In certain examples, the contrast agent source 140 is connected to the first fluid port 115 through the check valve 165. Similarly, the saline source 145 can be connected to the rotary manifold 105 through the second fluid source 120. In some examples, the saline source 145 is connected to the second fluid port 120 through the check valve 170. The check valves 165, 170 are passive components that merely prevent any fluid from getting injected back into the fluid source containers from the rotary manifold 105. In certain examples, multiple fluid sources can be connected to the first fluid port 115 (or the second fluid port 120). In these examples, the multiple fluid sources can be metered to produce the desired fluid combination when drawn into the injector 135.

The patient delivery mechanism 150 can be connected to the rotary manifold 105 through the output port 125. In an example, the patient delivery mechanism 150 can be a catheter. In an example, selected fluidic connectivity between the injector port 110 and the first fluid port 115, the second fluid port 120, or the output port 125 can be provided by the rotary manifold 105. Selection of the desired fluidic connection can be made by rotating the dial 130.

In certain examples, the gas bubble detector 180 can be connected between the output port 125 and the patient delivery mechanism 150. In some examples, the gas bubble detector 180 is integrated into the output port 125 of the rotary manifold 105. In an example, the gas bubble detector 180 can be integrated into the injector port 110 to detect gas bubbles before they enter the rotary manifold. In this configuration, the gas bubble detector 180 can be configured to only sense gas bubbles when fluid is being ejected out of the injector 135, in order to minimize any false alarms when fluid is drawn into the injector 135. In yet another example, gas bubble detectors can be attached to or integrated into any combination of ports, including the injector port 110, the first fluid port 115, the second fluid port 145, and the output port 125 to assist in ensuring no gas is present in the entire system 100 during operation. The gas bubble detector 180 can detect gas bubbles in the fluid as the fluid is injected into the patient delivery mechanism 150. The gas bubble detector 180 can be connected to an audible and/or visual alerting mechanism to alert the operator of the presence of gas bubbles, which can be dangerous to a patient's health. The configuration and operation of the gas bubble detector 180 is described in more detail below in reference to FIGS. 5, 6A-B, and 8.

In an example, the rotary manifold 105 can include a pressure transducer port 155, which enables the connection of a pressure transducer 160 capable of monitoring pressures within a patient's body, such as blood pressure. Due to the sensitivity of the pressure transducer 160, the rotary manifold 105 can be configured to prevent connectivity (e.g., fluid transfer) between the pressure transducer port 155 and the injector port 110 or output port 125 when fluid is being injected into the patient delivery mechanism 150.

Rotary Manifold Examples

Figure 2A:
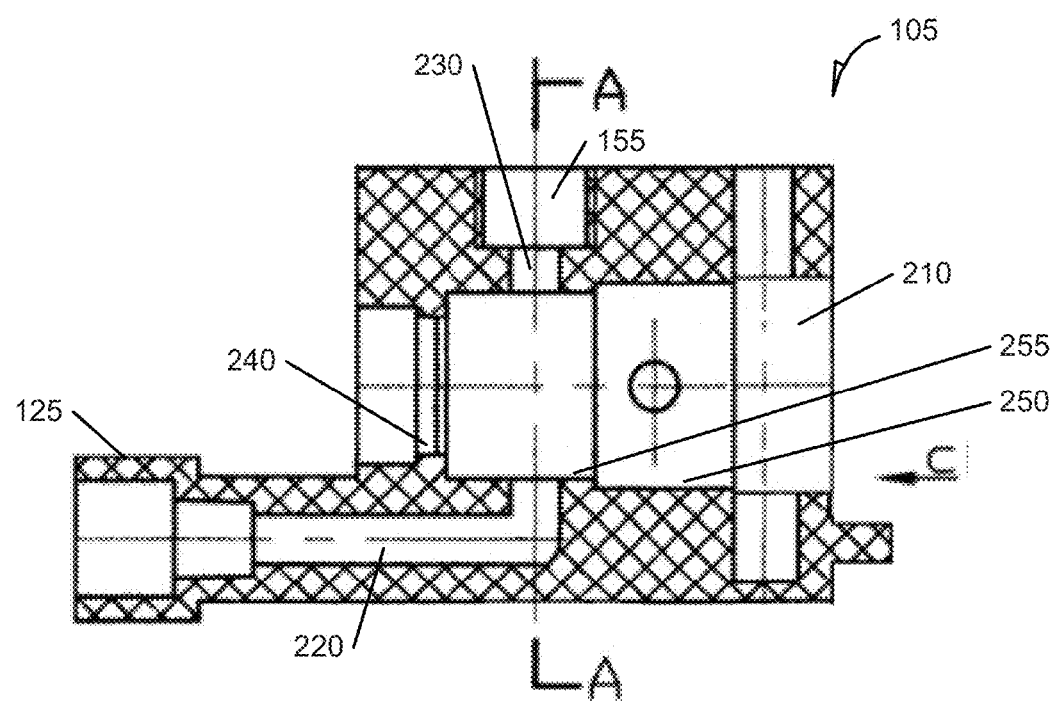
FIGS. 2A-D are line drawing illustrations of an example rotary manifold for connecting multiple fluid sources with a patient delivery mechanism.

FIGS. 2A-D are line drawing illustrations of an example rotary manifold for connecting multiple fluid sources with a patient delivery mechanism. FIG. 2A is a line drawing illustrating a cross-sectional view of an example rotary manifold 105. The rotary manifold 105 can include an output port 125, a pressure transducer port 155, a central cavity 210, an output passage 220, and a pressure passage 230. The output port 125 and the pressure transducer port 155 correspond to similarly labeled elements depicted in FIG. 1. These ports can provide both physical and fluidic connectivity to the rotary manifold 105. In an example, the ports can provide Luer Taper type connectors. A Luer Taper is a standardized system for small-scale fluid connection, which can provide leak-free connections between a male-taper fitting and a female fitting. In an example, the ports on the rotary manifold 105 will provide male-taper fittings to interconnect with female fittings on the fluid sources 140, 145, injector 135, and patient delivery mechanism 150.

In an example, the output port 125 is coupled to the central cavity 210 by the output passage 220. The central cavity 210 can contain a valve stem that provides selective fluidic connectivity to the output passage 220 and other fluid or pressure passages, such as the pressure passage 230. The pressure passage 230 couples the pressure transducer port 155 to the central cavity 210.

In an example, the central cavity 210 can be stepped providing different diameters 250, 255 in association with different fluid passages (e.g., diameter 255 in association with output passage 220 and pressure passage 230). An example central cavity 210 can also include a retention flange 240, which can be used to secure the valve stem into the central cavity 210. In an example, the retention flange 240 can be used to provide a snap-fit connection between the central cavity 210 and a valve stem.

Figure 2B:
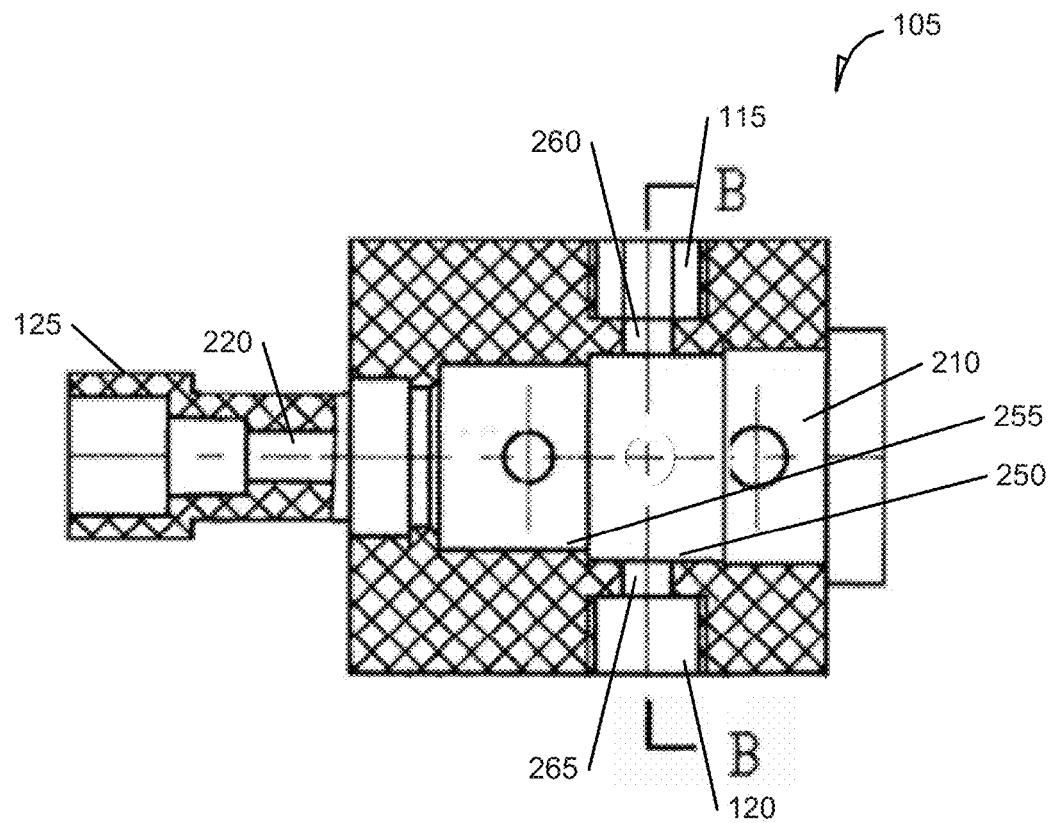

FIG. 2B is a line drawing illustrating a cross-sectional view of the rotary manifold 105, according to an example. The rotary manifold 105 depicted in FIG. 2B can include the first fluid port 115, the second fluid port 120, the output port 125, the central cavity 210, the output passage 220, a first fluid passage 260, and a second fluid passage 265. In an example, the first fluid port 115 can be coupled to the central cavity 210 by the first fluid passage 260. The second fluid port 120 can also be coupled to the central cavity 210 by the second fluid passage 265. In an example, the first fluid passage 260, in combination with the valve stem (not shown), can provide fluidic connection between the first fluid port 115 and the injector port 110. Similarly, the second fluid passage 265, in combination with the valve stem, can provide fluidic connection between the second fluid port 120 and the injector port 110.

Figure 2C:
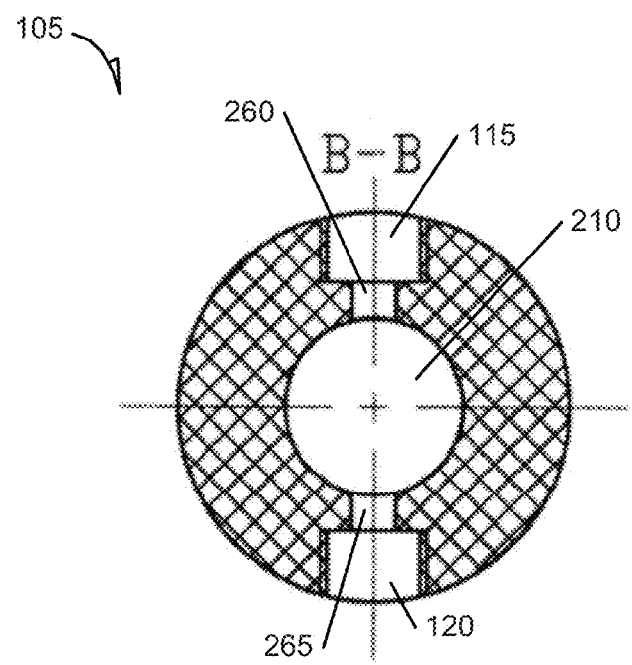

FIG. 2C is a line drawing illustrating a cross-sectional elevation B-B of an example rotary manifold 105. The cross-section of the rotary manifold 105 depicted in FIG. 2C includes the first fluid port 115, the second fluid port 120, the first fluid passage 260, the second fluid passage 265, and the central cavity 210.

Figure 2D:
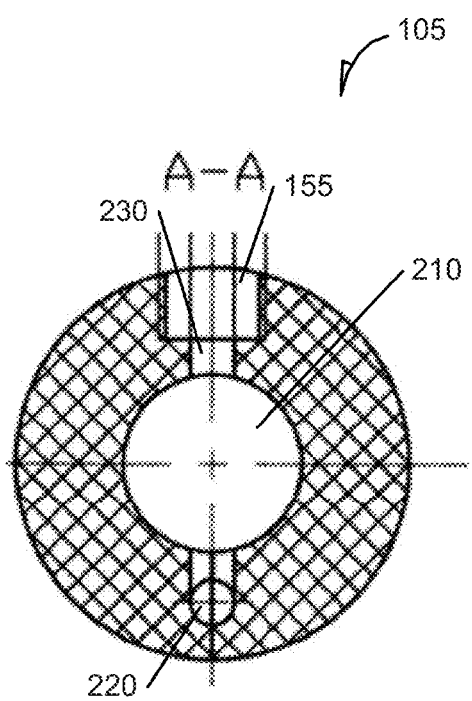

FIG. 2D is a line drawing illustrating a cross-sectional elevation C-C of an example rotary manifold 105. The cross-section of the rotary manifold 105 depicted in FIG. 2D includes the pressure transducer port 155, the pressure passage 230, the output passage 220, and the central cavity 210.

Figure 3A:
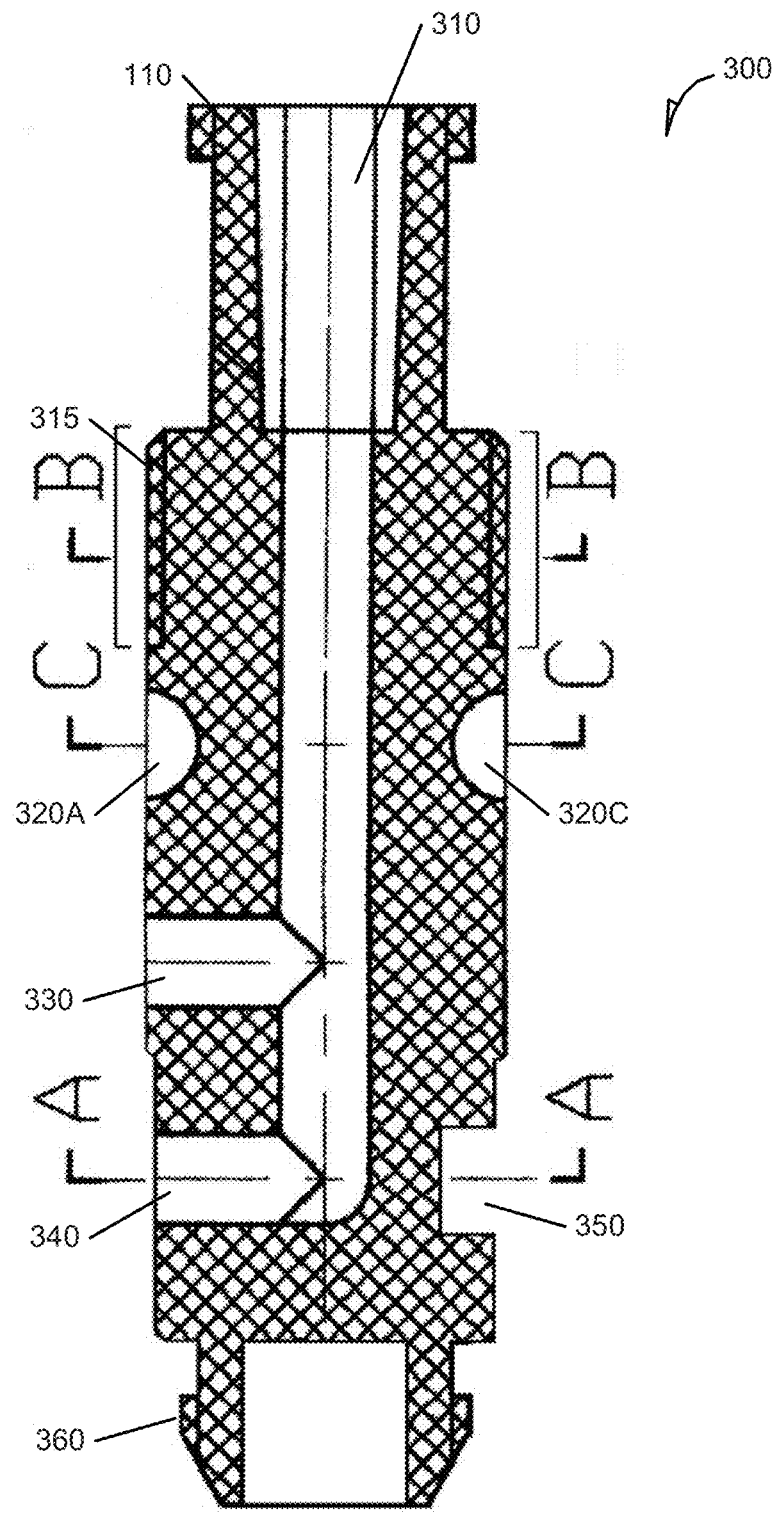
FIGS. 3A-D are line drawing illustrations of an example rotary valve stem for using in a rotary medical manifold.

FIGS. 3A-D are line drawing illustrations of an example valve stem for use in a rotary medical manifold. FIG. 3A is a line drawing illustrating a longitudinal cross-section of an example valve stem 300 for use in a rotary manifold 105. The valve stem 300 can include an injector port 110, a central fluid passage 310, a plurality of ribs 315 (see FIG. 3C), a plurality of detent positions 320A, 320C (collectively referred to as 320), a first perpendicular fluid passage 330, a second perpendicular fluid passage 340, a semicircular pressure passage 350, and a distal end 360.

In an example, the central fluid passage 310 provides the main fluid route between the injector port 110 and the first fluid port 115, the second fluid port 120, or the output port 125. Connecting to the central fluid passage 310 can be two additional fluid passages (e.g., the first perpendicular fluid passage 330 and the second perpendicular fluid passage 340) configured to selectively couple the first fluid port 115, the second fluid port 120, and the output port 125 to the central fluid passage 310. In an example, the fluid port that is connected depends on the rotational position of the valve stem 110.

The detent positions 320 can each correspond to a position that connects one of the fluid ports 115, 120, 125 with the central fluid passage 310. For example, in a first detent position 320A, the first fluid port 115 can be connected through the first perpendicular passage 330 to the central fluid passage 310. In this first detent position 320A, none of the other ports (e.g., second fluid port 120, output port 125, or the pressure transducer port 155) are connected to the central passage 310. In a second detent position 320B (not shown in FIG. 3A), the second fluid port 120 can be connected through the first perpendicular passage 330 to the central fluid passage 310. In a third detent position 320C, the output port 125 can be connected through the second perpendicular passage 340 to the central fluid passage 310. In this third detent position, the injector 135 connected to the injector port 110 can inject fluid into the central fluid passage 310, through the second perpendicular fluid passage 340, and out of the rotary manifold 105 through output passage 220 and the output port 125.

In an example, regardless of the rotational position of the valve stem 300, the semicircular pressure passage 350 does not have a fluidic connection to the central fluid passage 310. Consequently, the pressure transducer 160 cannot be directly coupled to the injector 135. The lack of a fluidic connection between the injector port 110 and the pressure transducer port 155 prevents the pressure transducer 160 from being exposed to high pressures that can be generated by the injector 135.

Figure 3B:
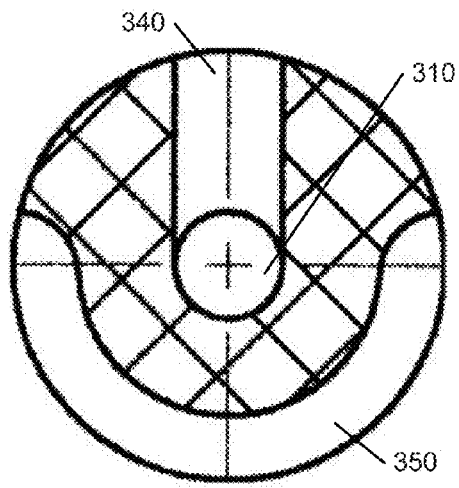

FIG. 3B is a line drawing of a cross-section A-A of an example valve stem 300 that can be used in a rotary manifold 105. The cross-section of the valve stem 300 depicted in FIG. 3B includes the central fluid passage 310, the second perpendicular fluid passage 340, and the semicircular pressure passage 350. This example highlights the lack of connectivity between the semicircular pressure passage 350 and the central fluid passage 310.

Figure 3C:
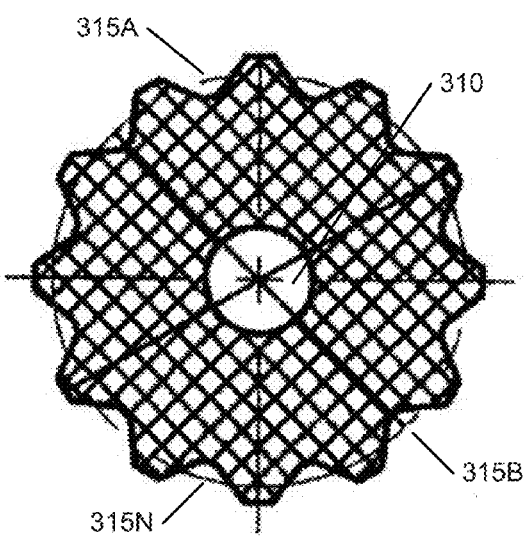

FIG. 3C is a line drawing of a cross-section B-B of an example valve stem 300 that can be used in a rotary manifold 105. The cross-section of the valve stem 300 depicted in FIG. 3C includes the central fluid passage 310 and the ribs 315A . . . 315N (collectively referred to as ribs 315). In an example, the dial 130 can be coupled to the valve stem 300 by the ribs 315.

Figure 3D:
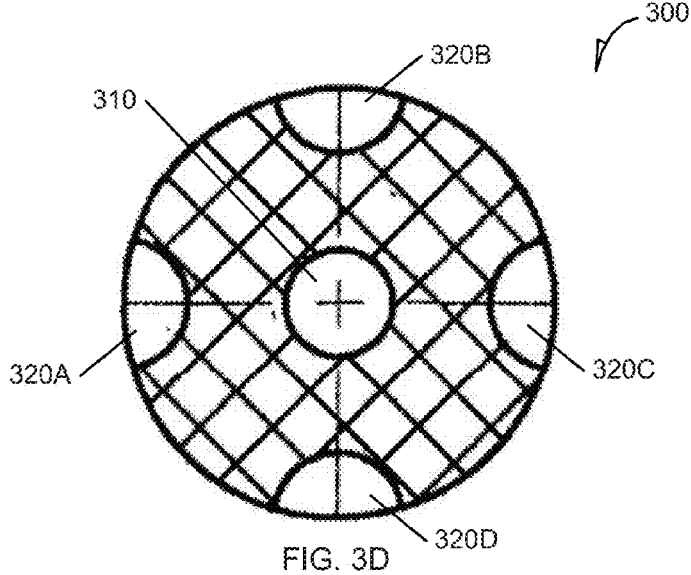

FIG. 3D is a line drawing of a cross-section C-C of an example valve stem 300 that can be used in a rotary manifold 105. The cross-section of the valve stem 300 depicted in FIG. 3D includes the central fluid passage 310 and the detent positions 320. In this example, each detent position 320A-320D is separated by ninety (90) degrees of rotation. In another example, the detent positions 320 can be oriented in different rotational positions, such as 0 degrees (320A), 60 degrees (320B), 120 degrees (320C), and 270 degrees (320D). In an example, the detent positions 320 can be aligned with each of the rotational positions associated with the first fluid port 115, the second fluid port 120, and the output port 125. In certain examples, a third fluid port can be included within the same plane as the first fluid port 115 and second fluid port 120, but in a different rotational position. In some examples, the valve stem 300 can include less than four detent positions or more than four detent positions, depending upon the number of fluid ports and output ports.

Figure 4A:
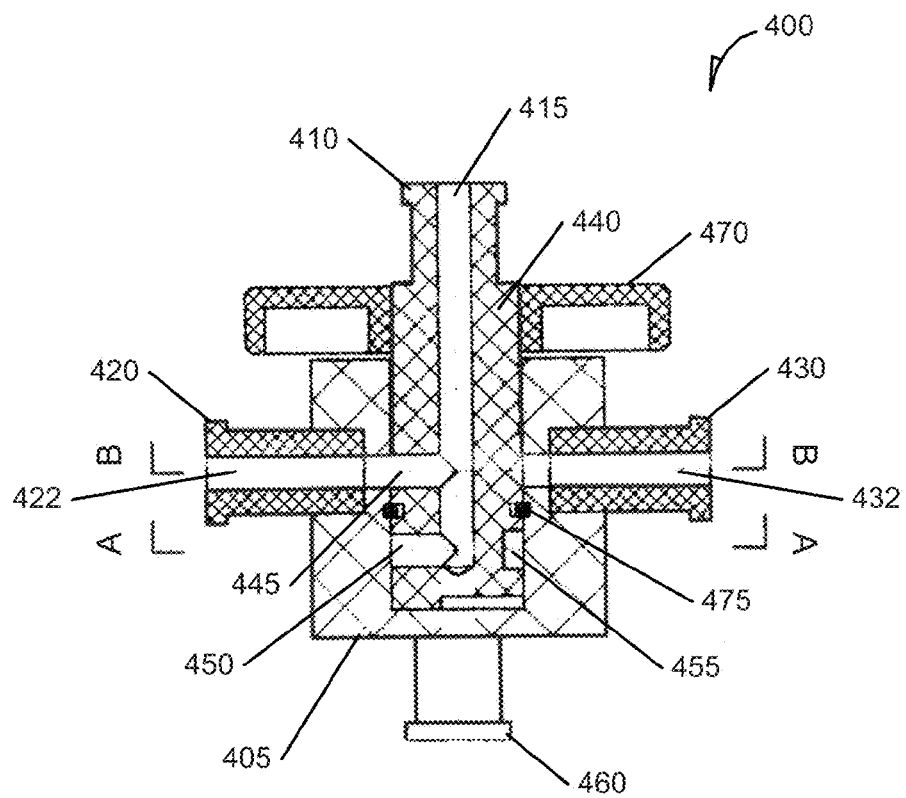
FIGS. 4A-D are line drawing illustrations of an example rotary medical manifold.

FIGS. 4A-D are line drawing illustrations of an example rotary medical manifold. FIG. 4A is a line drawing illustrating a cross-sectional view of an example rotary manifold 400. In this example, the rotary manifold 400 can include a manifold body 405, an injector port 410, a central fluid passage 415, a first fluid port 420, a second fluid port 430, a valve stem 440, an output port 460, and a dial 470. In an example, the first fluid port 420 can include a first fluid passage 422. The first fluid passage 422 can connect to the first perpendicular fluid passage 445 when the valve stem 440 is in a first rotational position, such as the position illustrated in FIG. 4A. The second fluid port 430 can include a second fluid passage 432. In an example, the valve stem 440 can be rotated to a second rotational position to align the first perpendicular passage 445 with the second fluid passage 432 to provide fluidic connectivity between the injector port 410 and the second fluid port 430. Note, the first and second rotation positions described in this example are merely relative positions and are not intended, in this context, to describe absolute positions. For example, in another example the first rotational position could be used to describe when the first perpendicular passage 445 is aligned with the second fluid passage 432. The valve stem 440 can also include a second perpendicular fluid passage 450 and a semicircular pressure passage 455. In an example, the rotary manifold 400 can include a snap ring retention device 475 to hold the valve stem 440 into the rotary manifold body 480.

Figure 4B:
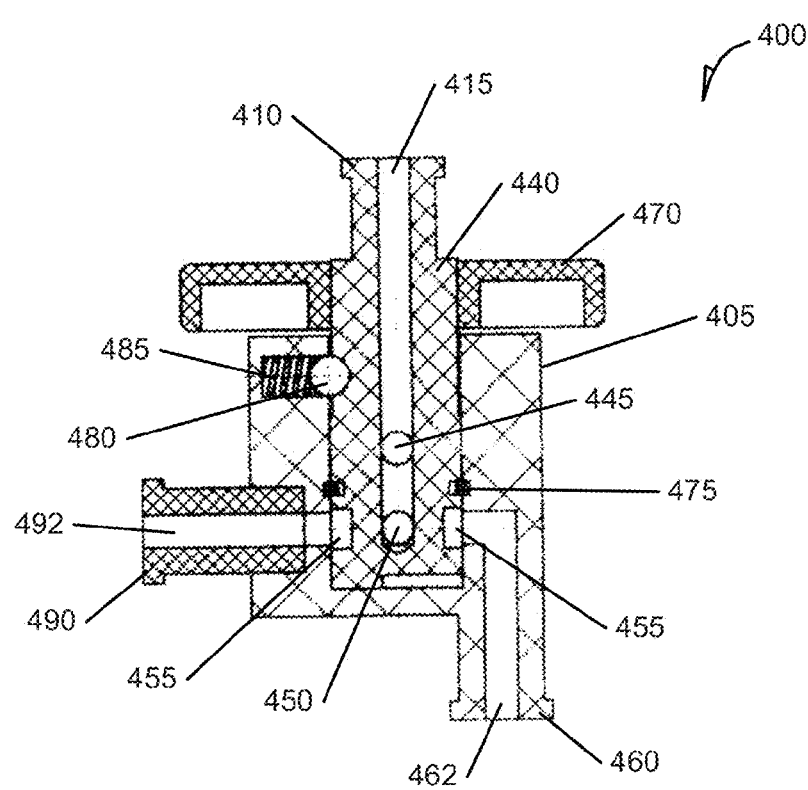

FIG. 4B is a line drawing illustrating a cross-sectional view of an example rotary manifold 400. In this example, the rotary manifold 400 can include the manifold body 405, the injector port 410, the central fluid passage 415, the valve stem 440, the output port 460, the dial 470, a detent ball 480, a detent bias member 485, and a pressure transducer port 490. In an example, the pressure transducer port can include a pressure passage 492 that can couple to a semicircular pressure passage 455 cut into the outer periphery of the valve stem 440. In this example, the semicircular pressure passage 455 is aligned in the same vertical plane as the second perpendicular fluid passage 450. However, as depicted in FIG. 4A, at least in this example, the second perpendicular fluid passage 450 and the semicircular pressure passage 455 do not intersect. In this example, the semicircular pressure passage 455 is shown providing a fluidic connection between the pressure transducer port 490 and the output port 460 through the pressure passage 492 and the output passage 462.

In an example, the second perpendicular fluid passage 450 can be rotated into alignment with the output passage 462 to provide fluidic connection between the injector port 410 and the output port 460, through the central fluid passage 415.

Rotation of the valve stem 440 within the rotary manifold body 405 can be accomplished using the dial 470. The detent ball 480 in conjunction with the detent bias member 485 can provide positive stops at each functional rotational position of the valve stem 440. Functional rotational positions can include those positions that enable fluidic connection between the injector port 410 and any one of the first fluid source port 420, the second fluid source port 430, or the output port 460. In certain other examples, additional functional rotational positions can include rotational positions that provide fluidic connection between additional fluid or waste ports (not shown) and the injector port 410.

In this example, the semicircular pressure passage 455 provides fluidic connectivity between the pressure transducer port 490 and the output port 460 in all of the functional rotational positions, except when the injector port 410 is connected to the output port 460. In this example, when the output port 460 is connected to the injector port 410 the pressure transducer port 490 is sealed off from the rest of the ports.

Figure 4C:
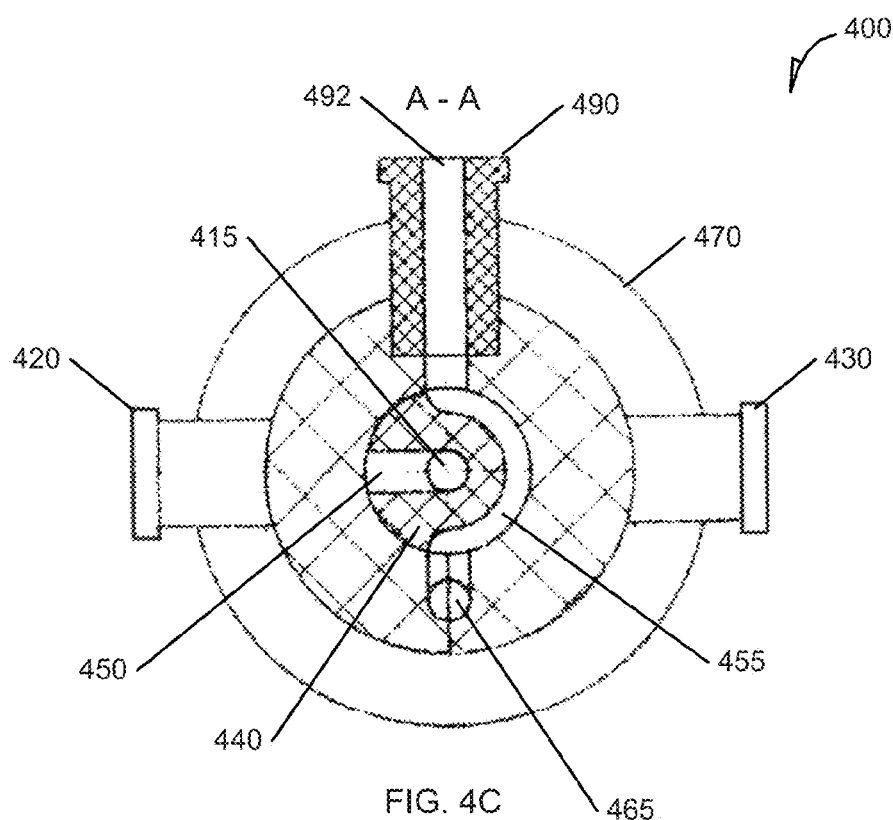

FIG. 4C is a line drawing illustrating section A-A of an example rotary manifold 400. The cross-section A-A of the rotary manifold 400 includes the central fluid passage 415, the first fluid source port 420, the second fluid source port 430, the valve stem 440, the second perpendicular fluid passage 450, the semicircular pressure passage 455, the output passage 465, the dial 470, the pressure transducer port 490, and the pressure passage 492.

In this example, the valve stem 440 is in a rotational position connecting the pressure transducer port 490 with the output passage 465 through the semicircular pressure passage 455. In this position, a pressure transducer connected to the pressure transducer port 490 can monitor pressures within a patient's body. This example also illustrates that the central fluid passage 415 cannot be coupled to the output port 460 in this rotational position (e.g., when the output port 460 (through the output passage 465) is coupled to the pressure transducer port 490.

Figure 4D:
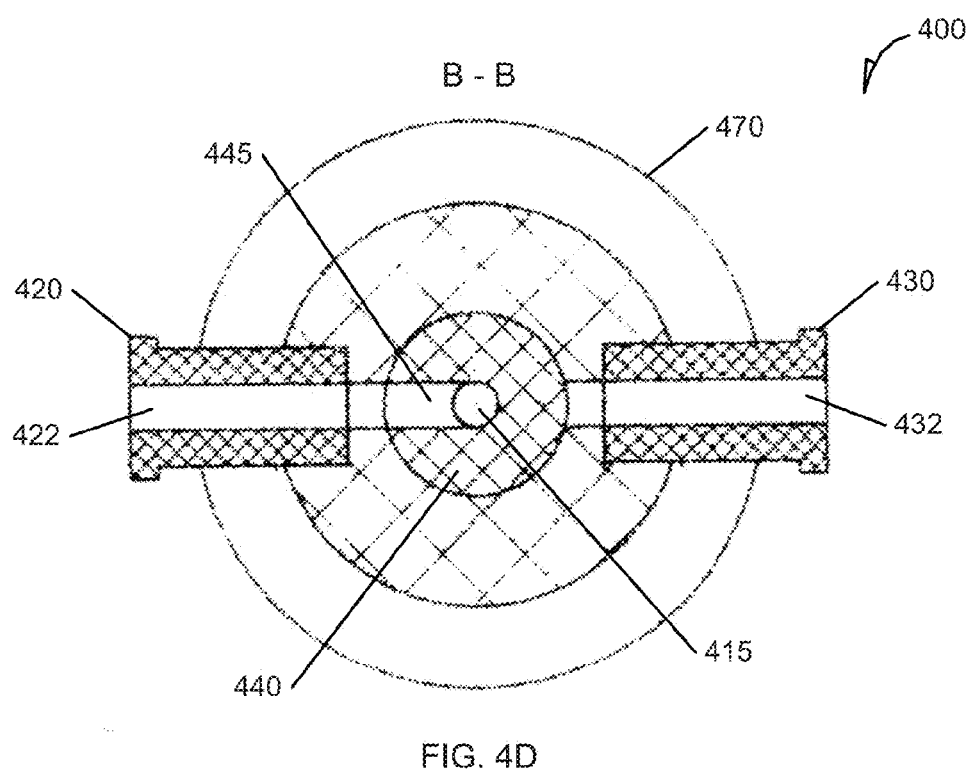

FIG. 4D is a line drawing illustrating section B-B of an example rotary manifold 400. The cross-section B-B of the rotary manifold 400 includes the central fluid passage 415, the first fluid source port 420, the first fluid passage 422, the second fluid source port 430, the second fluid passage 432, the valve stem 440, the first perpendicular fluid passage 445, and the dial 470. In this example, the valve stem 440 is in a rotational position connecting the first fluid source port 420 with the central fluid passage 415 through the first fluid passage 422 and the first perpendicular fluid passage 445. The valve stem 440 can be rotated, 180 degrees in this example, to couple the second fluid source port 430 with the central fluid passage 415.

In the example depicted by FIGS. 4A-4B, the rotary manifold 400 includes three functional rotational positions, a first, a second and a third rotational position. The first rotational position, depicted by FIG. 4D, couples the first fluid source port 420 with the injector port 410 through the central fluid passage 415 and the first perpendicular fluid passage 422. The second rotation position, 90 degrees counter-clockwise from the first rotational position, couples the output port 460 with the injector port 410 through the central fluid passage 415 and the second perpendicular fluid passage 450. The third rotational position, 90 degrees counter-clockwise from the second rotational position, couples the second fluid source port 430 with the injector port 410 through the central fluid passage 415 and the first perpendicular fluid passage 445. In this example, at both the first and the third rotational positions, the output port 460 is coupled to the pressure transducer port 490 through the semicircular pressure passage 455.

Gas Bubble Detector Examples

Figure 5:
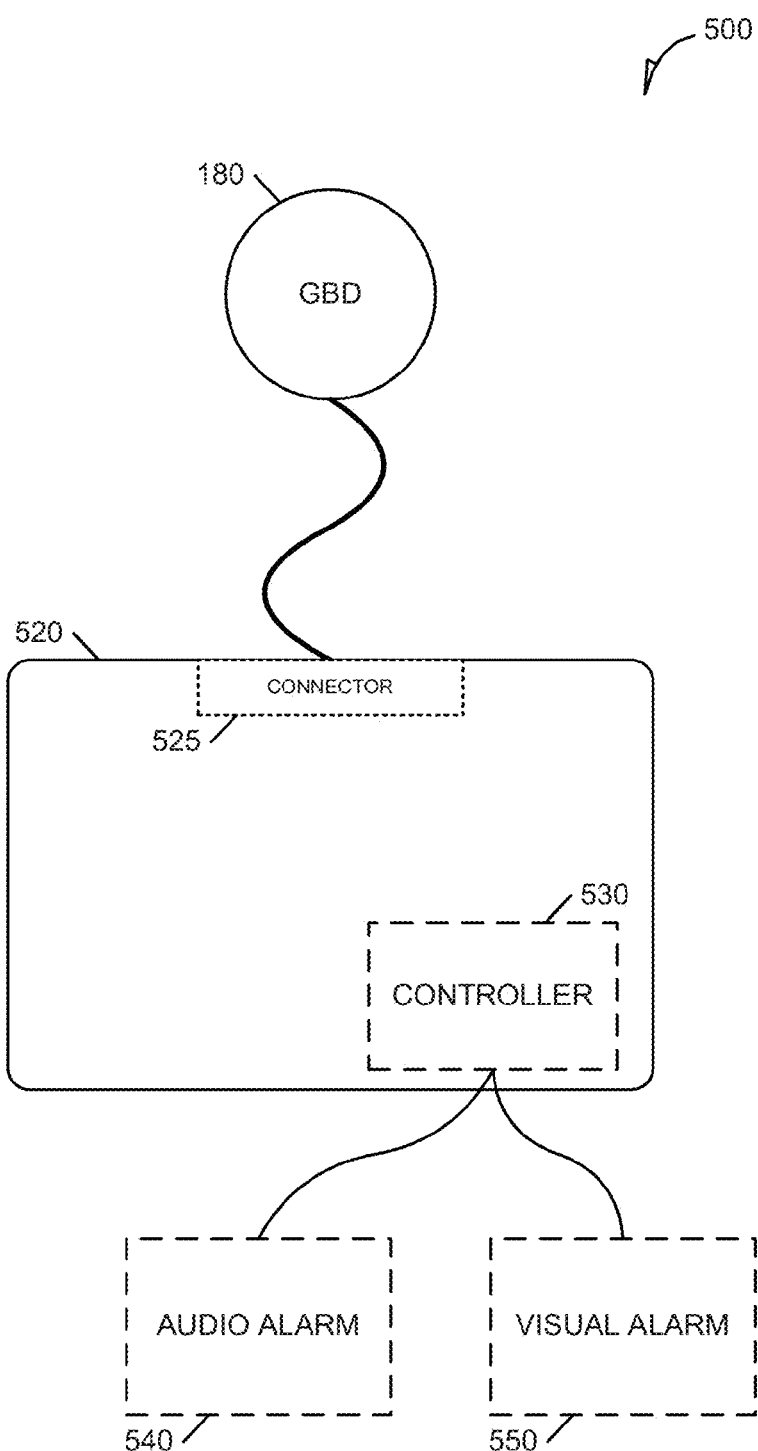
FIG. 5 is a block diagram illustrating an example system for detecting gas bubbles within a fluid.

FIG. 5 is a block diagram illustrating an example system 500 for detecting gas bubbles within a fluid. The system 500 can include a gas bubble detector 180 coupled to a computer 520. In certain examples, the computer 520 can include a connector 525 and a controller 530. In some examples, the system 500 also includes a audio alarm 540 and a visual alarm 550. In an example, the gas bubble detector can be communicatively coupled to the connector 525 within the computer 520. The controller 530 can include programming (software or programmable hardware, such as a field programmable gate array (FPGA)) for controlling the gas bubble detector 180 and sending signals to the audio alarm 540 and/or the visual alarm 550.

Figure 6A:
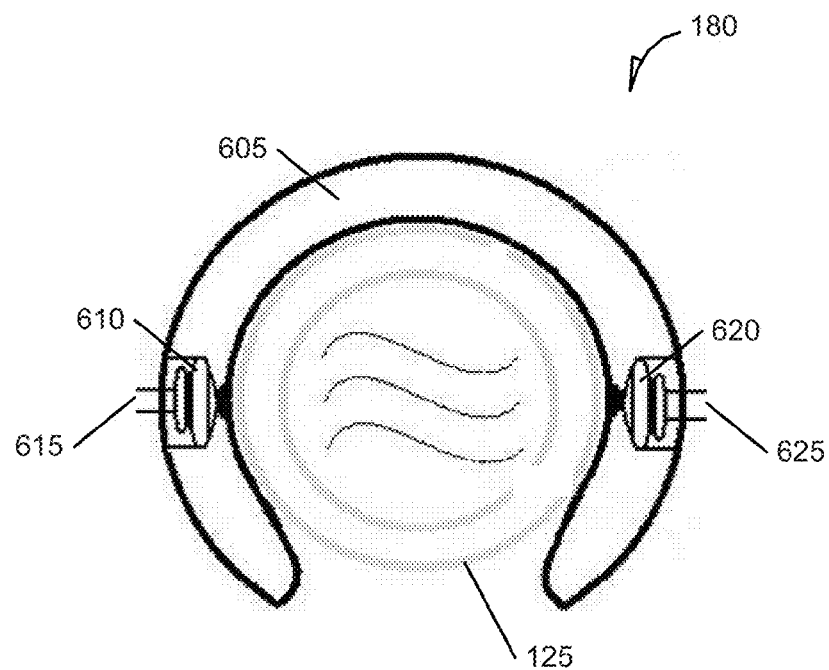
FIGS. 6A-B is a block diagram illustrating an example gas bubble detection apparatus.
Figure 6B:
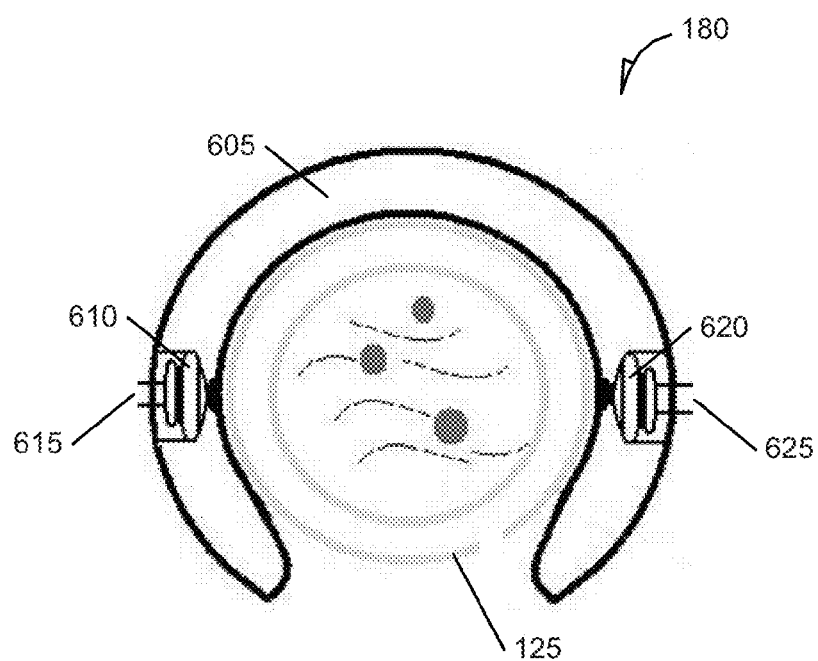

FIGS. 6A-B is a block diagram illustrating an example gas bubble detection device 180. The gas bubble detector 180 can include a sensor body 605, an emitter 610, and a detector 620. In an example the emitter 610 can include electrical connections 615 that can be used to control the light emitted from the emitter 610. The detector 620 can also include electrical connections 625 for controlling the detector 620. The emitter electrical connections 615 and the detector electrical connections 625 can be communicatively coupled to the computer 520. The detector electrical connections 625 can also be used to transmit information regarding the light being received by the detector 620 to the computer 520 for analysis.

FIG. 6A is a block diagram illustrating an example gas bubble detection device 180 with normal fluid flow within the output port 125. Under the conditions depicted by FIG. 6A the detector 620 can receive steady uninterrupted light waves from the emitter 610. FIG. 6B is a block diagram illustrating an example gas bubble detection device 180 with gas bubbles in the fluid flow with the output port 125. In the example depicted by FIG. 6B, the detector 620 will detect interruptions in the light waves received from the emitter 610, providing an indication of gas in the fluid.

Method of Use Examples

Figure 7:
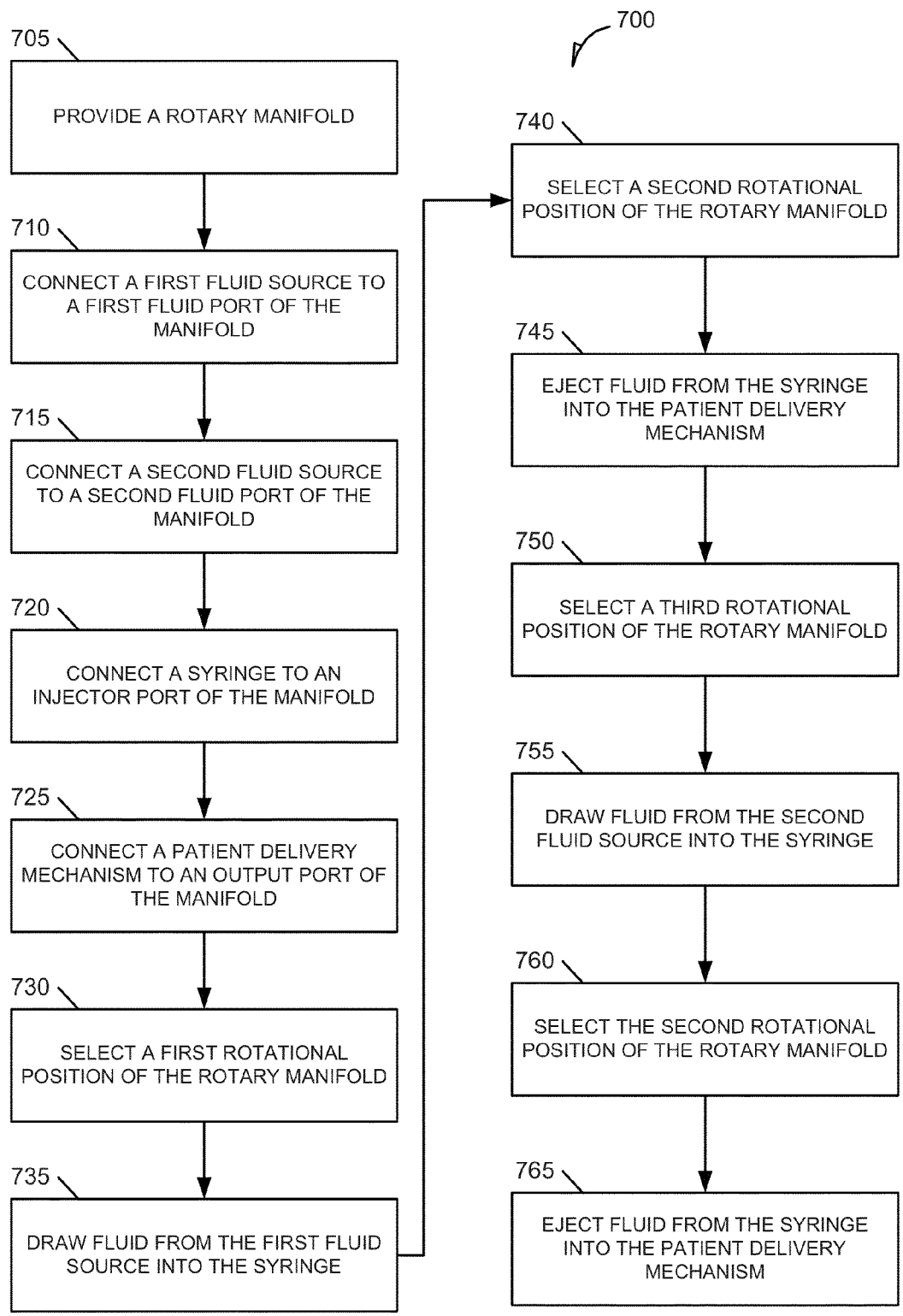
FIG. 7 is a flowchart illustrating an example method of using a rotary medical manifold.

FIG. 7 is a flowchart illustrating an example method 700 of using a rotary medical manifold. The method 700 can include providing a rotary manifold at 705, connecting a first and second fluid source to the manifold at 710, 715, connecting a syringe to an injector port at 720, connecting a patient delivery mechanism to an output port at 725, selecting a first rotational position at 730, drawing fluid from the first fluid source at 735, selecting a second rotational position at 740, ejecting fluid from the syringe at 745, selecting a third rotational position at 750, drawing fluid from the second fluid source at 755, selecting the second rotational position at 760, and ejecting fluid from the syringe at 765.

The method 700 can begin at 705 with a physician or technician providing a rotary manifold 105. For the remainder of this example, the healthcare worker performing the operations will be referred to as the technician, but could also be a physician, a nurse, a radiologist, or any qualified healthcare worker. At 710, the method 700 continues with the technician connecting a first fluid source, such as a contrast agent 140, to the first fluid port 115. Next at 715, the method 700 continues with the technician connecting a second fluid source, such as a saline source 145, to the second fluid port 120. Operations 710 and 715 can also include the technician connecting one-way check valves (165, 170) between the rotary manifold 105 and the fluid sources (140,145), respectively.

At 720, the method 700 continues with the technician connecting a syringe 135 (or similar injection device) to the injector port 110 of the rotary manifold 105. At 725, the method 700 can continue with the technician connecting a patient delivery mechanism, such as a catheter 150, to the output port 125. The technician can also optionally connect a gas bubble detector 180 to the output port 125 prior to connecting the catheter 150.

At 730, the method 700 continues with the technician selecting a first rotational position using the dial 130. The dial 130 can include a visual indicator for each rotational position, such as a number for symbol representative of the type of fluid or operation to be completed in each position. For example, in the angiography example, the first position can be indicated with "C" for contrast agent. Additional rotational positions can also include visual indictors, such as "S" for saline and "O" for output. Alternatively, the visual indications on the dial 130 can simply be numbers 1, 2, 3, 4, etc. . . . for each position.

At 735, the method 700 continues with the technician drawing fluid from the contrast source 140 into the syringe 135. The process of drawing fluid into the syringe 135 can be performed in a manner similar to drawing fluid into a syringe without a manifold (e.g., simply pulling back on the plunger of the syringe to create a vacuum within the syringe and drawing fluid into the syringe).

At 740, the method 700 continues with the technician selecting a second rotational position of the rotary manifold 105 using the dial 130. In this example, the second rotational position connects the injector port 110 with the output port 125. Once in the second rotation position, the method 700 can continue at 745 with the technician ejecting fluid from the syringe 135 into the catheter 150 through the rotary manifold 105.

At 750, the method 700 can continue with the technician selecting a third rotational position of the rotary manifold 105 using the dial 130. Rotating the dial 130 can turn the valve stem 300 coupled to the dial 130. In this example, the third rotational position connects the injector port 110 with the second fluid port 120. At 755, the method 700 can continue with the technician drawing fluid from the saline source 145 (e.g., the second fluid source) into the syringe 135.

AT 760, the method 700 can continue with the technician moving the dial 130 back to the second rotational position to re-connect the injector port 110 with the output port 125. Back in the second rotational position, the method 700 can complete at 765 with the technician ejecting fluid from the syringe 135 into the catheter 150. In this example, at 765, the fluid ejected into the catheter 150 is from the second fluid source (e.g., saline source 145).

Method 700 represents one example method of using the rotary manifold 105 during a medical procedure, such as angiography. However, any combination of these operations can be performed to inject various fluids that can be connected to the rotary manifold 105. Additionally, a rotary manifold with one or more additional ports can be used if more than two fluids are involved in the procedure or if a waste port for disposing of excess fluid is required.

As discussed above, an optional pressure transducer 160 can be connected to the pressure transducer port 155 to monitor pressures within the patient's body during a procedure, such as the one outline in method 700. For example, the rotary manifold 105 can be configured to enable the pressure transducer 160 to monitor pressures in the first and third rotational positions, as described in reference to method 700.

In certain example procedures, it may be desirable to deliver a combination of multiple fluids to a patient with a single injection. In these examples, it is possible to use the rotary manifold 105 to draw multiple fluids into the injection 135. For example, the rotary manifold 105 can be rotated to couple the first fluid source 140 with the injection 135. At this first position, the technician can draw the desired amount of the first fluid into the injector 135. Next, the rotary manifold 105 can be rotated to couple the second fluid source 145 with the injector 135. At this second position, the technician can draw the desire amount of the second fluid into the injector 135, creating the desired combination. Finally, the rotary manifold 105 can be rotated to couple the output port 125 with the injector 135 and the combined fluid can be injected into the patient delivery mechanism 150. Note, in an example rotary manifold that includes additional fluid ports, additional fluids can be included in the combination.

Figure 8:
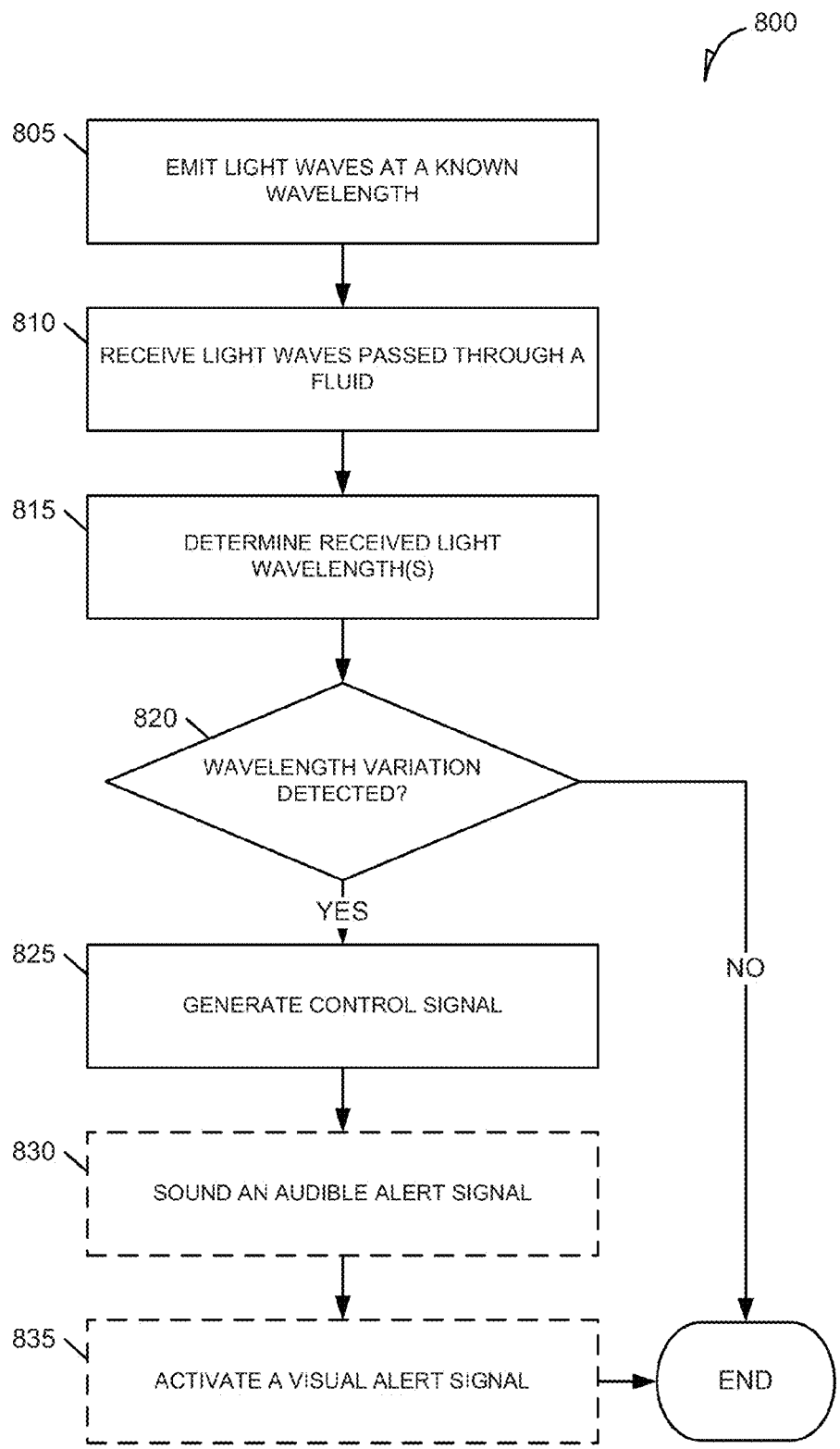
FIG. 8 is a flowchart illustrating an example method of detecting gas bubbles within a fluid.

FIG. 8 is a flowchart illustrating an example method 800 of detecting gas bubbles within a fluid. The method 800 can include emitting light waves at a known wavelength at 805, receiving light waves passed through a fluid at 810, determining received light wavelengths at 815, detecting any variation in the received light wavelengths at 820, and generating a control signal at 825. Optionally, method 800 can include sounding an audible alert signal at 830 and activating a visual alert signal at 835.

The method 800 can begin at 805 with the emitter 610 emitting light waves at a known wavelength. In an example, the light waves can be passed through a fluid exiting the rotary manifold 105 at the output port 125. At 810, the method 800 continues with the detector 620 receiving light waves passed through the fluid exiting the output port 125. In an example, the detector 620 sends information indicative of the light waves received to the computer 520 for analysis. At 815, the method 800 can continue with the computer 520 determining the wavelengths of light received by the detector 620. At 820, the method 800 continues with the computer 520 determining whether there are any wavelength variations detected within the light received by the detector 620. If wavelength variation is detected, then the method 800 can continue at 825 with the controller 530 generating a control signal. In some examples, the method 800 continues at 830 with the controller 530 sending a control signal to an audio alarm 540 to sound an audible alert signal. The audible alert signal can inform that technician of the potential of gas bubbles entering the patient delivery mechanism 150. In certain examples, the method 800 continues at 835 with the controller 530 sending a control signal to a visual alarm. The control signal can activate a visual alert signal, which can inform the technician of the potential of gas bubbles entering the patient delivery mechanism 150.

As discussed above, the gas bubble detector 180 can be integrated into the output port 125. The gas bubble detector 180 can also be coupled to or integrated with the injector port 110, the first fluid port 115, or the second fluid port 120. In some examples, multiple gas bubble detectors can be integrated into the rotary manifold 105, further enhancing a technician's ability to prevent gas bubbles from entering the patient delivery mechanism 150.

The above detailed description includes references to the accompanying drawings, which form a part of the detailed description. The drawings show, by way of illustration, specific embodiments in which the invention can be practiced. These embodiments are also referred to herein as "examples." Such examples can include elements in addition to those shown and described. However, the present inventors also contemplate examples in which only those elements shown and described are provided.

All publications, patents, and patent documents referred to in this document are incorporated by reference herein in their entirety, as though individually incorporated by reference. In the event of inconsistent usages between this document and those documents so incorporated by reference, the usage in the incorporated reference(s) should be considered supplementary to that of this document; for irreconcilable inconsistencies, the usage in this document controls.

In this document, the terms "a" or "an" are used, as is common in patent documents, to include one or more than one, independent of any other instances or usages of "at least one" or "one or more." In this document, the term "or" is used to refer to a nonexclusive or, such that "A or B" includes "A but not B," "B but not A," and "A and B," unless otherwise indicated. In the appended claims, the terms "including" and "in which" are used as the plain-English equivalents of the respective terms "comprising" and "wherein." Also, in the following claims, the terms "including" and "comprising" are open-ended, that is, a system, device, article, or process that includes elements in addition to those listed after such a term in a claim are still deemed to fall within the scope of that claim. Moreover, in the following claims, the terms "first," "second," and "third," etc. are used merely as labels, and are not intended to impose numerical requirements on their objects.

The above description is intended to be illustrative and not restrictive. For example, the above-described examples (or one or more aspects thereof) may be used in combination with each other. Other embodiments can be used, such as by one of ordinary skill in the art upon reviewing the above description. The Abstract is provided to comply with 37 C.F.R. §1.72(b), to allow the reader to quickly ascertain the nature of the technical disclosure. It is submitted with the understanding that it will not be used to interpret or limit the scope or meaning of the claims. Also, in the above Detailed Description, various features may be grouped together to streamline the disclosure. This should not be interpreted as intending that an unclaimed disclosed feature is essential to any claim. Rather, inventive subject matter may lie in less than all features of a particular disclosed embodiment. Thus, the following claims are hereby incorporated into the Detailed Description, with each claim standing on its own as a separate embodiment. The scope of the invention should be determined with reference to the appended claims, along with the full scope of equivalents to which such claims are entitled.

What is claimed is:

1. An apparatus comprising:
    a manifold body including a central cavity, an output port, a first fluid port, and a second fluid port;
    a valve stem, adapted to slidably engage the central cavity, the valve stem including:
        a single central longitudinal fluid passage connected to an injector port;
        a first perpendicular fluid passage intersecting the central longitudinal fluid passage at a first longitudinal location to selectively provide fluidic transport between the central longitudinal fluid passage and the output port when the valve stem is in a first rotational position; and
        a second perpendicular fluid passage intersecting the central longitudinal fluid passage at a second longitudinal location different than the first longitudinal location to selectively provide fluidic transport between the central longitudinal fluid passage and a selected one of the first and second fluid ports, fluidic transport to the first fluid port is provided when the valve stem is in a second rotational position and fluidic transport to the second fluid port is provided when the valve stem is in a third rotational position; and
    wherein a proximal portion of the valve stem is adapted to enable selective rotation of the valve stem within the central cavity to rotatably selectively provide fluidic transport between the central longitudinal fluid passage and one of the first fluid port, the second fluid port, and the output port.

2. The apparatus of claim 1, wherein the manifold body includes a self-biasing mechanism to positively position the valve stem in the first, the second, or the third rotational position, the self-biasing mechanism including:
    a plurality of detent cavities positioned to correspond with each of the first, second, and third rotational positions;
    a detent ball configured to inhibit rotational movement of the valve stem when positioned within one of the detent cavities; and
    a detent bias member configured to press the detent ball into one of the detent cavities.

3. The apparatus of claim 1, wherein the valve stem comprises a stepped cylinder with a first cylinder diameter at the output port position, and a second cylinder diameter at the first and second fluid port position.

4. The apparatus of claim 1, including a pressure transducer port;
    wherein the manifold body includes the pressure transducer port selectively coupled in fluid communication with the output port and configured to be coupled to a pressure transducer to permit monitoring of fluid pressure at the output port; and
    wherein the valve stem includes a transducer fluid passage.

5. The apparatus of claim 4, wherein the transducer fluid passage comprises a semi-circular groove in a perimeter of the valve stem.

6. The apparatus of claim 4, wherein the transducer fluid passage is configured to inhibit or prevent exposing the pressure transducer to fluid pressure from the injector port.

7. The apparatus of claim 1, wherein the valve stem is adapted to snap-fit into the central cavity of the manifold body.

8. The apparatus of claim 1, including a gas bubble detector coupled to the output port and configured to detect a gas bubble in a fluid exiting the output port.

9. The apparatus of claim 8, wherein the gas bubble detector is configured to detect a gas bubble by detecting a change in a light wave passing through the fluid exiting the output port.

10. A fluid delivery system, the system comprising:
    a manifold configured to selectively interconnect, using a central rotary valve, an injector port with a first fluid port, a second fluid port, and a patient delivery port, the central rotary valve having a single central longitudinal fluid passage, the single central longitudinal fluid passage connecting to the first and second fluid ports via a first perpendicular fluid passage at a first longitudinal location, the single central longitudinal fluid passage connecting to the patient delivery port via a second perpendicular fluid passage at a second longitudinal location different from the first longitudinal location;
    wherein the first fluid port is configured to be coupled to a contrast fluid source;
    wherein the second fluid port is configured to be coupled to a saline fluid source; and
    wherein the injector port is configured to be coupled to an injection device and the injection device is configured to:
        draw fluid from the contrast source when the central rotary valve is in a first rotational position;
        draw fluid from the saline source when the central rotary valve is in a second rotational position; and
        output fluid through the patient delivery port when the central rotary valve is in a third rotational position.

11. The fluid delivery system of claim 10, further including a pressure transducer connected to a pressure transducer port on the manifold.

12. The fluid delivery system of claim 11, wherein the manifold is configured to interconnect the patient delivery port with the pressure transducer port when the central rotary valve is in any one of the first or second rotational positions.

13. The fluid delivery system of claim 10, including a gas bubble detector coupled to the patient delivery port.

14. The fluid delivery system of claim 13, wherein the gas bubble detector is configured to detect gas bubbles in the fluid exiting the patient delivery port by detecting changes in light waves passed through the fluid.

15. The fluid delivery system of claim 10, further comprising at least one of the contrast source, the saline source, or the injection device.

16. A method comprising:
providing a rotary manifold with a central rotary valve, an injector port, an output port, a first fluid port, and a second fluid port, the central rotary valve including a single central longitudinal fluid passage connected to the injector port, the single central longitudinal fluid passage connecting to the first and second fluid ports via a first perpendicular fluid passage at a first longitudinal location, the single central longitudinal fluid passage connecting to the patient delivery port via a second perpendicular fluid passage at a second longitudinal location different from the first longitudinal location;
connecting a first fluid source to the first fluid port;
connecting a second fluid source to the second fluid port;
connecting a syringe to the injector port of the rotary manifold;
connecting a patient delivery mechanism to the output port;
selecting a first rotational position, of the central rotary valve, the first position interconnecting the first fluid source and the syringe;
drawing fluid from the first fluid source into the syringe;
selecting a second rotational position, of the central rotary valve, the second position interconnecting the syringe and the output port;
ejecting the fluid from the first fluid source from the syringe into the patient delivery mechanism through the output port;
selecting a third rotational position, of the central rotary valve, the third position interconnecting the syringe and the second fluid source;
drawing fluid from the second fluid source into the syringe;
selecting the second rotational position, of the central rotary valve;
ejecting the fluid from the second fluid source from the syringe into the patient delivery mechanism through the output port.

17. The method of claim 16, including monitoring pressure from the patient delivery mechanism at a pressure transducer port coupled to the patient delivery mechanism through a pressure passage in the central rotary valve.

18. The method of claim 17, wherein the second position of the central rotary valve seals off the pressure transducer port from the output port and the injector port.

19. The method of claim 16, wherein each of the first, second, and third rotational positions are 90 degrees of rotation apart.

20. The method of claim 16, wherein the ejecting the fluid includes monitoring the output port for gas bubbles.

21. The method of claim 20, wherein the monitoring the output port for gas bubbles includes detecting changes in the wavelengths of light passed through the fluid ejected into the patient delivery mechanism.

* * * * *

UNITED STATES PATENT AND TRADEMARK OFFICE
CERTIFICATE OF CORRECTION

PATENT NO. : 8,478,385 B2  Page 1 of 1
APPLICATION NO. : 12/562996
DATED : July 2, 2013
INVENTOR(S) : Liu et al.

It is certified that error appears in the above-identified patent and that said Letters Patent is hereby corrected as shown below:

Title page, in column 1, under "(75) Inventors", line 2, delete "BeiJing" and insert --Beijing--, therefor Signed and Sealed this
Eighteenth Day of November, 2014

Michelle K. Lee
*Deputy Director of the United States Patent and Trademark Office*